United States Patent
Parks et al.

(10) Patent No.: US 9,116,122 B2
(45) Date of Patent: Aug. 25, 2015

(54) SURFACE PLASMON RESONANCE BIOSENSOR

(71) Applicants: Allen D. Parks, Spotsylvania, VA (US); Scott E. Spence, Fredericksburg, VA (US); Rose M. Hayden, King George, VA (US)

(72) Inventors: Allen D. Parks, Spotsylvania, VA (US); Scott E. Spence, Fredericksburg, VA (US); Rose M. Hayden, King George, VA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/184,661

(22) Filed: Feb. 19, 2014

(65) Prior Publication Data

US 2014/0333930 A1     Nov. 13, 2014

Related U.S. Application Data

(63) Continuation-in-part of application No. 13/135,974, filed on Jul. 6, 2011, now Pat. No. 8,674,688, which is a continuation-in-part of application No. 13/134,486, filed on Jun. 6, 2011, now Pat. No. 8,493,066.

(51) Int. Cl.
*G01N 21/55*     (2014.01)
*G01N 21/552*    (2014.01)

(52) U.S. Cl.
CPC ...... *G01N 21/553* (2013.01); *G01N 2201/0683* (2013.01)

(58) Field of Classification Search
USPC .......................................................... 324/244
See application file for complete search history.

(56) References Cited

U.S. PATENT DOCUMENTS

| | | | |
|---|---|---|---|
| 4,160,269 A * | 7/1979 | Kramer et al. | 369/109.01 |
| 5,313,264 A * | 5/1994 | Ivarsson et al. | 356/73 |
| 7,429,735 B2 * | 9/2008 | Lueerssen et al. | 250/341.8 |
| 8,411,278 B2 | 4/2013 | Parks et al. | 356/540 |
| 8,493,066 B2 | 7/2013 | Parks | 324/244.1 |
| 8,520,214 B2 | 8/2013 | Parks et al. | 356/465 |
| 2010/0103421 A1 * | 4/2010 | Johansen et al. | 356/367 |
| 2010/0128275 A1 * | 5/2010 | Chau et al. | 356/445 |
| 2011/0001975 A1 * | 1/2011 | Razansky et al. | 356/445 |
| 2012/0314215 A1 | 12/2012 | Parks et al. | 356/364 |
| 2013/0050707 A1 | 2/2013 | Parks et al. | 356/450 |
| 2013/0155411 A1 | 6/2013 | Parks et al. | 356/450 |

OTHER PUBLICATIONS

Hosten et al., Obesrvation of the Spin Hall Effect of Light via Weak Measurements, Science, V. 319, Feb. 8, 2008, p. 787-790.*
X. Pan et al., "Sensitive optical biosensors for unlabeled targets: a review", *Analytica Chemica Acta* 620, Aug. 26, 2008. http://www.bme.umich.edu/labs/fanlab/files/prj__2008/sensitive_optical_biosensors_for_unlabeled_targets_a_review.pdf.

(Continued)

*Primary Examiner* — Thomas F Valone
(74) *Attorney, Agent, or Firm* — Gerhard W. Thielman, Esq.

(57) ABSTRACT

An optical biosensor is provided for detecting a bio-molecular sample by Goos-Hänchen (GH) enhancement of Aharonov-Albert-Vaidman (AAV) amplification to a surface plasmon resonance (SPR) detector. The sensor includes pre- and post-selection polarizers respectively upstream and downstream of a right-isosceles prism with a metal film and a liquid medium disposed on a diagonal side of the prism. Laser light passes through the first polarizer, reflects at the film, passes through the second polarizer and is detected with a shift determined by a pointer estimator to indicate the sample.

8 Claims, 1 Drawing Sheet

(56) References Cited

OTHER PUBLICATIONS

Y. Aharonov et al., "How the Result of a Measurement of a Component of the Spin of a Spin-½ Particle Can Turn Out to be 100", *Phys Rev. Ltrs*, 60 (1988), 14 1351-54. http://www.tau.ac.il/~vaidman/1vhp/m8.pdf.

Y. Aharonov et al., "Properties of a quantum system . . . " *Phys. Rev. A*, 41 (1990) http://pra.aps.org/pdf/PRA/v41/i1/p11_1.

A. Parks et al., "Observation and measurement of an optical AAV effect" *Proc. Roy. Soc. Lond. A*, 454 2997-3008 (1990).

B. Liedberg et al.; "Surface Plasmon Resonance for Gas Detection and Biosensing", *Sensors & Actuators* 4, 299-304 (1983).

V. F. Goos et al., "Ein neuer und fundamentaler Versuch zur Totalreflexion", *Ann. Physik* 6 (1) 333-346 (1947). http://onlinelibrary.wiley.com/doi/10.1002/andp.19474360704/pdf.

X. Yin et al., Goos-Hänchen shift surface plasmon resonance sensor, *Appl. Phys. Lett.* 89, 261108 (2006).

G. Jayaswal et al. "Weak measurement of the Goos-Hänchen shift", *Opt. Lett.* 38, 1232-1234 (2013) . http://arxiv.org/pdf/1301.0788v4.pdf.

I. M. Duck et al., "The sense in which a 'weak measurement' of a spin-½ particle's spin component yields a value 100" *Phys. Rev. D* 40 2112-17 (1989). http://prd.aps.org/pdf/PRD/v40/i6/p2112_1.

\* cited by examiner

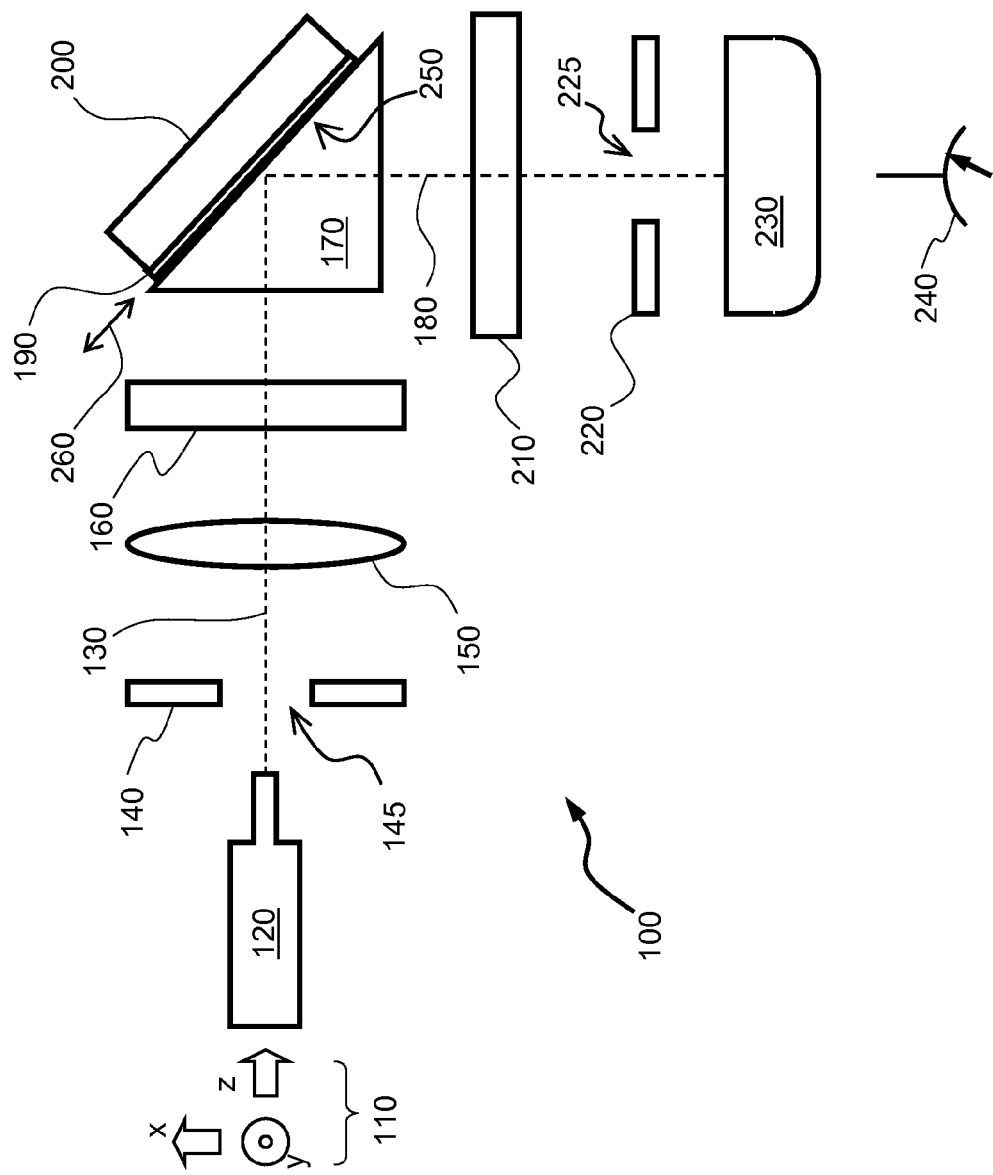

SURFACE PLASMON RESONANCE BIOSENSOR

CROSS REFERENCE TO RELATED APPLICATION

The invention is a Continuation-in-Part, claims priority to and incorporates by reference in its entirety U.S. patent application Ser. No. 13/135,974 filed Jul. 6, 2011, published as U.S. Patent Application Publication 2012/0314215 and assigned Navy Case 100288, which claims priority to and incorporates by reference in its entirety U.S. patent application Ser. No. 13/134,486 filed Jun. 6, 2011, issued as U.S. Pat. No. 8,493,066 and assigned Navy Case 99670.

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to a biosensor based on amplification by weak quantum measurements. In particular, the, biosensor uses the Aharonov-Albert-Vaidman (AAV) effect to amplify the surface plasmon resonance (SPR) enhanced Goos-Hänchen (GH) effect (hereafter, this biosensor can be referred to as the hybrid SPR/GH/AAV biosensor, or more simply as the hybrid biosensor.

The GH effect constitutes the small undetectable splitting of a polarized laser beam in response to total internal reflection of the beam. A thin gold film, disposed upon the surface of a total internal reflection prism, provides an SPR enhancement of the GH effect, i.e., the film increases the splitting of the incident laser beam. This splitting is proportional to the concentration of bio-molecules adhering to the gold film, i.e., the greater the concentration, the greater the splitting. Although this splitting is small for low concentrations of bio-molecules, application of the AAV effect can amplify the splitting. The hybrid sensor thereby enables the detection of extremely small heretofore undetectable concentrations of bio-molecules.

Optical biosensors are used to identify unknown biological hazards to facilitate effective mitigation upon discovery. A summary of such conventional devices is presented by X. Fan et al., "Sensitive Optical Biosensors for Unlabeled Targets: A Review", *Analytics Chemica Acta* 620, 8-26 (2008), available at http://www.bme.umich.edu/labs/fanlab/files/prj_13 2008/sensitive_optical_biosensors_for_u nlabeled_targets_a_review.pdf.

Signal amplification by the Aharonov-Albert-Vaidman (AAV) effect, has been used for measurement augmentation based on the weak value $A_w$ of a quantum mechanical observable operator $\hat{A}$. The AAV effect is described by Y. Aharonov at al., "How the Result of a Measurement of a Component of the Spin of a Spin—½ Particle Can Turn Out To Be 100", *Phys. Rev. Lett.* (1988) 60, 1351- 1354, available at http://www.tau.ac.il/~vaidman/lvhp/m8.pdf or else http://prl.aps.org/pdf/PRL/v60/i14/p1351_1 for details.

Further information on the AAV effect can be found in Y. Aharonov et al. "Properties Of A Quantum System During The Time Interval Between Two Measurements", *Phys. Rev. A* 41, 11-20 (1990) available for example at http://xa.yimg.com/kq/groups/2385221/367896748/name/Aharonovweaknessmeasureme ntPhysRevA.41.11.pdf, and A. Parks, D. Cullin, and D. Stoudt, "Observation and Measurement of an Optical Aharonov-Albert-Vaidman effect", *Proc. R. Soc. Lond.* A 454, 2997-3008 (1998), available at http://www.jstor.org/stable/53338 and at http://rspa.royalsocietypublishing.org/content/454/1979/2997.full.pdf.

Optical sensors using surface plasmon resonance (SPR) have been used for the direct detection of bio-molecules at surfaces since the mid-1980s. Such SPR sensors are generally comprised of three integrated portions: the optical detection component (ODC), the liquid management component (LMC), and the collection surface component (CSC). More specifically, typical SPR sensors are total internal reflection devices with a thin gold or silver film deposited upon the surface of a high dielectric medium. This represents the front interface, and that associated with the other side of the film is the rear interface.

When a beam of monochromatic transverse magnetic light is incident from the high dielectric medium upon the metallic film interface at an angle θ greater than or equal to the critical angle such that the light's magnetic field vector is parallel to the interface surface, an optically induced longitudinal oscillation of free electrons in the metal film resonantly transfers energy from the light to the surface plasmon wave propagating along the interface. This interaction is sensitive to changes in the reflective index of the medium at the rear interface (e.g., produced by bio-molecules introduced by the LMC that adhere to a metallic film which serves as the CSC) and yields a reduction in the intensity of the reflected light as a response to changes in the reflective index.

Consequently, the presence of bio-molecular species at the rear interface is heralded by changes in the light intensity reflected at an angle at or near θ. Such optical SPR sensors are generally referred to as attenuated total reflection (ATR) devices. The SPR phenomenon is described by B. Liedberg et al., "Surface Plasmon Resonance for Gas Detection and Biosensing", *Sensors and Actuators* 4, 299-304 (1983).

SUMMARY

Conventional biosensors yield disadvantages addressed by various exemplary embodiments of the present invention. In particular, a biosensor is provided for an optical biosensor for detecting a cellular sample deposited in a liquid medium. The biosensor includes a laser source, a collimating lens, pre- and post-selection polarizers, an optical right-isosceles prism, a metal film disposed between the prism and the liquid medium, a photon detector and a pointer estimator.

The laser source emits a photon beam in an axial direction into an ambient medium; a collimating lens disposed perpendicular to the axial direction. to concentrate the beam. The pre-selection polarizer is disposed perpendicular to the beam to polarize the beam by angle α. The optical right-isosceles prism has a dielectric constant greater than the ambient medium and includes incident and exodus sides perpendicular to each other and an opposite diagonal side.

The beam enters the prism through the incident side, reflects by the diagonal side and exits towards a lateral direction through the exodus side. The metal film is disposed on the diagonal side to provide surface plasmon resonance (SPR) amplification of a Goos-Hächen (GH) effect. The liquid medium is disposed along the metal film opposite the diagonal side with the sample adjacent the metal film.

The post-selection polarizer is disposed perpendicular to the lateral direction to polarize the beam by angle β. The photon detector detects photons from the beam. The pointer estimator measures a mean intensity and determines a GH shift $\Delta_{GH}$ that translates from a zero position corresponding to the mean intensity absent the sample on the metal film.

In additional embodiments, the detector obtains weak measurement:

$$\Gamma_w = \frac{\langle \psi_f | \hat{\Gamma} | \psi_i \rangle}{\langle \psi_f | \psi_i \rangle} \gg 1 \tag{1}$$

of a polarization difference operator $\hat{\Gamma}$, such that $|\psi_i\rangle$ and $|\psi_f\rangle$ denote respective pre- and post-selective states, thereby enabling Aharonov-Albert-Vaidman (AAV) amplification. In yet further embodiments, wherein the the pre-selection polarizer has angle $$\alpha = \frac{\pi}{4}$$

and the post-selection polarizer has angle $\beta = -\alpha + \epsilon$, where deviation angle is defined as $0 < \epsilon \ll 1$, and the weak measurement equals cotangent of the deviation angle such that $\Gamma_w = \cot \epsilon$.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which:

FIG. is a schematic view of an exemplary hybrid biosensor

DETAILED DESCRIPTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

In accordance with a presently preferred embodiment of the present invention, the components, process steps, and/or data structures may be implemented using various types of operating systems, computing platforms, computer programs, and/or general purpose machines. In addition, those of ordinary skill in the art will readily recognize that devices of a less general purpose nature, such as hardwired devices, or the like, may also be used without departing from the scope and spirit of the inventive concepts disclosed herewith. General purpose machines include devices that execute instruction code. A hardwired device may constitute an application specific integrated circuit (ASIC) or a field programmable gate array (FPGA) or other related component.

An exemplary optical detection component (ODC) for a biosensor applies Aharonov-Albert-Vaidman (AAV) amplification to the surface plasmon resonance (SPR) enhanced Goos-Hänchen (GH) effect enables detection of extremely small concentrations of bio-molecules deposited on the rear interface of the metallic film. The GH effect is described by F. Goos et al., "Ein Neuer und Fundamentaler Versuch Zur Totalreflexion", *Ann. Physik* 6, 1, 333-346 (1947) available at http://onlinelibrary.wiley.com/doi/10.1002/andp.19474360704/pdf.

Two important experiments recently reported in the physics literature support the concept of a simple optical hybrid biosensor with a detection sensitivity greatly exceeding that of conventional SPR biosensors. The first of these experiments showed that SPR greatly enhances the GH effect for ATR as reported by X. Yin et al., "Goos-Hänchen shift surface plasmon resonance sensor", *Appl. Phys. Lett.* 89, 261108 (2006). The second experiment demonstrated that the AAV effect can be used to amplify the GH effect, as reported in G. Jayaswal at al., "Weak Measurement of the Goos-Hänchen shift", *Optics Letters* 38, 1232-1234 (2013) available at http://arxiv.org/pdf/1301.0788v4.pdf.

The GH effect can be combined with SPR enhancement to further refine sensitivity. While the law of reflection that declares "the angle of incidence equals the angle of reflection" is true for plane waves (e.g., geometric optics), this statement is only approximately valid for (transversely finite) light beams that undergo total internal reflection at a dielectric interface. In the example under disclosure, the center of the reflected beam is spatially translated in the plane of incidence relative to that of the reflected beam. This extremely small translation results from an exponentially decreasing evanescent wave induced by the partial penetration of the beam's electromagnetic field across the interface.

The associated Poynting vector is static and directed along the interface so that the reflected energy flux is spatially translated by a small distance with respect to the reflected geometric optics beam, i.e., the reflected beam exhibits the GH effect by undergoing a GH translation. If the incident beam is a superposition of linear polarizations parallel to the plane of incidence (p polarization) as well as orthogonal to it (s polarization), then the p(s) polarized photons yield a reflected beam, which is translated a small distance $D_p$ ($D_s$). In general, translation in perpendicular is much less than parallel to the incidence plane, or $D_s \ll D_p$.

A relatively simple experimental apparatus employed in Yin (2006) demonstrates that the increased energy penetration induced in ATR devices by SPR greatly enhances the otherwise extremely small GH translation distances. There a 980 nm wavelength laser with ~200 μm beam waist was used to excite SPR in an ATR device containing glass and water media separated by a gold film 42 nm thick. The resonance incidence angle was fine-tuned by rotating the ATR using a motorized rotational stage and a fluidic cell was mounted on top of the ATR in order to infuse chemicals along the rear interface of the gold film. The GH shift was determined by light intensity collected by a detector.

Infusing various concentrations of sodium chloride (NaCl) in an inert aqueous solution into the fluidic cell at the rear interface, shifts the associated GH by 39 μm$<\Delta_{GH}=D_p-D_s<$44 μm varying linearly with concentration or reflectivity index at room temperature. Sensitivity is denoted in refractive index units (RIU). This yields a sensitivity of $1.82 \times 10^{-8}$ RIU/nm. The resolvable range reflective index change of $\sim 4 \times 10^{-7}$ RIU in this experiment was dictated by the ~20 nm position resolution of the photon intensity detector. Observations indicate that:

(i) these results were non-optimal and could be improved by using more advanced detection techniques and by fine tuning the laser wavelength and the gold film thickness to enhance the resonance/light beam coupling; and (ii) because the GH effect relates to a phase change, the effect provides a simpler high performance phase-sensitive alternative to more complex interferometric methods.

AAV Amplification of the GH shift further enhances signal sensitivity. In Jayaswal (2013), the AAV effect was used to greatly amplify the extremely small GH shifts. This was accomplished using an apparatus based upon the simple AAV effect canonical architecture. In particular, a laser source emitted a collimated Gaussian beam of 826 nm wavelength classically intense laser light beam with a 260 µn beam waist $\Delta x$. After transiting a pre-selection linear polarizer with first angle setting $\alpha$, the beam traversed a total internal reflection (TIR) prism that produced small lateral GH displacements $D_p$ and $D_s$ for the p and s polarization components of the light.

The beam then passed through a post-selection linear polarizer with second angle setting $\beta$, and the emerging light was collected by a detector. The mean position of the intensity profile of the light at the detector (i.e., the "pointer" of the apparatus) yielded the GH shift $\Delta_{GH}=D_p-D_s$. When first angle $$\alpha = \frac{\pi}{4}$$

and second angle $\beta=-\alpha+\epsilon$, $\epsilon \ll 1$, then $\Delta_{GH}$ was amplified by the large factor $$\cot\varepsilon \approx \frac{1}{\varepsilon}.$$

To observe this result, the following conditions can be set:
(a) for $|p\rangle$ and $|s\rangle$ to be the orthonormal photon linear polarization states (here, polarizations s and p respectively correspond to vertical y-direction and horizontal x-direction polarizations, in the laboratory Cartesian reference frame 110 shown in the FIG.);
(b) for z to be the direction of the beam 130;
(c) for x to be the direction of pointer displacement; and
(d) for $|\phi\rangle$ to be the initial Gaussian pointer state with zero mean (i.e., $\langle \phi | \hat{x} | \phi \rangle = 0$.

For these conditions, $\hat{x}$ is the position operator in the x-direction); and $$|\psi_i\rangle = \cos\alpha |s\rangle + \sin\alpha |p\rangle \quad (2)$$

denotes the pre-selected polarization state as a wave function for a photon based on the first angle setting.

After transiting the pre-selection polarizer, but prior to passing through the prism, the system is in the tensor product state:

$$|\Phi\rangle = |\phi\rangle |\psi_i\rangle. \quad (3)$$

where $|\phi\rangle$ denotes a Gaussian pointer. Interaction of a photon with the prism yields the entangled state $|\Theta\rangle$:

$$|\Theta\rangle = e^{-\frac{i}{\hbar}\gamma \hat{\Gamma} \hat{p}_x} |\psi_i\rangle |\phi\rangle, \quad (4)$$

where Y is the coupling strength between the photon and the prism, $\hat{p}_x$ is the pointer momentum in the x-direction, $i=\sqrt{-1}$ denotes imaginary unit, $$\hbar = \frac{h}{2\pi}$$

is the reduced Planck's constant (also called Dirac's constant), and $\hat{\Gamma}$ represents the polarization difference operator denoted by:

$$\hat{\Gamma} = |s\rangle\langle s| - |p\rangle\langle p|. \quad (5)$$

Upon post-selection of the polarization state can be expressed as:

$$|\psi_f\rangle = \cos\beta |s\rangle + \sin\beta |p\rangle, \quad (6)$$

based on the second angle setting. Consequently, the entangled state in eqn. (4) becomes:

$$|\Psi\rangle = \langle \psi_f | e^{-\frac{i}{\hbar}\gamma \hat{\Gamma} \hat{p}_x} | \psi_i \rangle |\phi\rangle, \quad (7)$$

where $|\Psi\rangle$ denotes the state of the pre- and post-selected system.

In order for the measurement to be weak, the weakness conditions must be satisfied. These weakness conditions involve inequalities described in Parks (1998) and by I. Duck et al., "The Sense In Which A 'Weak Measurement' Of A Spin-½ Particle's Spin Component Yields A Value 100", *Phys. Rev. D* 40, 2112-2117 (1989) available at http://prd.aps.org/pdf/PRD/v40/i6/p2112_1. For strength Y simultaneously satisfying the associated inequalities:

$$\gamma \ll 2\Delta x |\Gamma_w|^{-1} \text{ and } \gamma \ll 2\Delta x \min_{n=2,4\ldots} \left\{1, |\Gamma_w|^{\frac{1}{n-1}}\right\}, \quad (8)$$

where $\Delta x$ is the uncertainty in a photon's position in the lateral x-direction, then the corresponding measurement is a weak measurement.

This weak measurements provides that:

$$e^{-\frac{i}{\hbar}\gamma \hat{\Gamma} \hat{p}_x} \approx \hat{1} - \frac{i}{\hbar}\gamma \hat{\Gamma} \hat{p}_x, \quad (9)$$

and eqn. (7) can be approximated as:

$$|\Psi\rangle \approx \langle \psi_f | \psi_i \rangle \hat{S}(\gamma \Gamma_w) |\phi\rangle, \quad (10)$$

such that the measurement:

$$\Gamma_w = \frac{\langle \psi_f | \hat{\Gamma} | \psi_i \rangle}{\langle \psi_f | \psi_i \rangle} = \frac{\cos(\alpha+\beta)}{\cos(\alpha-\beta)}, \quad (11)$$

constitutes the weak value of polarization difference operator $\hat{\Gamma}$ and $$\hat{S}(\gamma \Gamma_w) \equiv e^{-\frac{i}{\hbar}\gamma \Gamma_w \hat{p}_x}, \quad (12)$$

is the pointer translation operator $\hat{S}$ defined by the action:

$$\langle x | \hat{S}(\gamma \cdot \Gamma_w) | \phi \rangle = \phi(x - \gamma \Gamma_w), \quad (13)$$

where x is the transverse lateral direction, and $\phi$ is the Gaussian pointer wavefunction.

The associated intensity profile in the x-direction is:

$$|\langle x|\Psi\rangle|^2 \approx |\langle \psi_f|\psi_i\rangle|^2 |\langle x|S(\gamma\Gamma_w)|\phi\rangle|^2 = |\langle \psi_f|\psi_i\rangle|^2 |\phi(x-\gamma\Gamma_w)|^2, \quad (14)$$

and corresponds to a broad single peaked Gaussian with its pointer position translated from its initial zero value to the new mean position:

$$\langle \Psi|\hat{x}|\Psi\rangle = \gamma\Gamma_w, \quad (15)$$

such that intensity pointer value as a mean position corresponds to the weak polarization measurement.

From Jayaswal (2013), one can determine that the coupling strength corresponds to:

$$\gamma = \frac{1}{2}\Delta_{GH}. \quad (16)$$

Consequently, if polarization angles $$\alpha = \frac{\pi}{4}$$

and $\beta = -\alpha\epsilon$, then the weak polarization difference operator $\Gamma_w = \cot\epsilon$, and eqn. (15) becomes:

$$\langle \Psi|\hat{x}|\Psi\rangle = \frac{1}{2}\Delta_{GH}\cot\epsilon, \quad (17)$$

such that the mean position corresponds to the GH shift.

When $0 < \epsilon \ll 1$, the pointer translation (i.e., the new x position of the peak intensity) can be made extremely large, thereby amplifying the GH shift $\Delta_{GH}$ by the factor of $$\frac{1}{2}\cot\epsilon \approx \frac{1}{2\epsilon}.$$

Thus, the AAV effect renders observable very small and otherwise unobservable GH shifts by measuring the large mean position $\langle \Psi|\hat{x}|\Psi\rangle$ and multiplying this state by $$\frac{2}{\cot\epsilon}$$

to obtain the GH shift:

$$\Delta_{GH} = \frac{2\langle \Psi|\hat{x}|\Psi\rangle}{\cot\epsilon} \approx 2\epsilon\langle \Psi|\hat{x}|\Psi\rangle, \quad (18)$$

such that $0 < \epsilon \ll 1$, as noted for large peak intensity.

Using their simple canonical AAV TIR apparatus and selecting $\epsilon = 0.01$ radian, the experimentalists in Jayaswal (2013) successfully demonstrated hundred-fold AAV effect amplifications of extremely small constraint $\Delta_{GH}$ values ranging from 2500 nm at a 42° incidence angle to 250 nm at a 46° incidence angle.

Hybrid AAV/GH/SPR Biosensors can thereby be synthesized. The afore-described analysis strongly indicates that a hybrid biosensor employing the AAV effect to amplify the SPR enhanced GH effect greatly outperforms the ability of standard SPR sensors to detect extremely small concentrations of bio-molecules collected by their CSC components corresponding to GH shifts much smaller than 10.4 μm.

The FIG. illustrates a schematic view 100 for such an exemplary biosensor. A compass rose 110 defines the Cartesian axes of the laboratory reference frame, i.e., x (up), y (out of page) and z (right) directions. A laser 120 emits photons in the z-direction to form a coherent light beam 130 that reaches a first slit screen 140 that includes an aperture 145 through which the beam 130 passes.

A lens 150 collimates the beam 130, which then passes through a pre-selection polarizer 160 to reach (at an angle greater than or equal to the associated critical angle) a TIR prism 170 comprising a high dielectric constant medium relative to the ambient environment. The prism 170 constitutes a right-isosceles prism configuration and reflects the incident light beam 130 along a surface opposite to and diagonal from sides that receive the incident beam 130 along the reflected exodus path 180. The prism 170 rotates the reference frame by —½·π (i.e., clockwise) following the beam 130 for the x (right) and z (down) directions along the path 180.

A thin gold or silver film 190 is deposited upon the prism 170 along its diagonal side and provides the SPR enhancement of the GH effect produced by the interaction between the laser beam 130 and the prism 170. A biological sample for detection is contained in a liquid and controlled by the LMC 200. The liquid is disposed adjacent to and disposed along the film 190 opposite the prism 170, and a portion of the biological sample within the liquid adheres to the film 190.

Upon reflection of the incident beam 130 by the prism 170, the reflected beam along the exodus path 180 passes through a post-selection polarizer 210, to encounter a second slit screen 220 and pass through its window 225. The photons in the reflected beam 180 reach a photon detector 230, which then responds to indicate a pointer shift to the mean intensity estimator 240. The detector 230 can preferably represent a charge coupled device (CCD) or a split detector. Mean intensity refers to the surface position on the detector 230 of the maximum or peak of the laser light's photon distribution along the x-axis. The zero position corresponds to the location on the detector 230 of the peak distribution without a GH shift. The SPR enhanced AAV amplification of the GH shift laterally translates the mean intensity away from the zero. The magnitude of this translation is proportional to the GH shift and depends upon the amount of the sample on the gold film 190.

As can be seen the sensor architecture in view 100, the simple canonical AAV amplifier used in Jayaswal (2013) can be used to amplify GH shift $\Delta_{GH}$ but modified to SPR enhance the GH effect via the thin gold film 190 attached to the rear of the TIR prism 170 and in front of the LMC 200. Consequently, the exemplary theory describes the properties of this hybrid sensor and its pointer position (i.e., the mean of the intensity profile at the detector 230 as determined by the pointer estimator 240) corresponds to the AAV amplified SPR enhanced GH shift $\Delta_{GH}$ when the pre- and post-selection polarizers 160 and 210 are set to angles $$\alpha = \frac{\pi}{4}$$

and $\beta = -\alpha + \epsilon$ for $0 < \epsilon \ll 1$ respectively. The polarization angle α is the twist rotation induced by the pre-selection polarizer 160 about (or around) the z axis of the beam 130 shown in the FIG. Looking from behind the laser 120 towards the pre-selection polarizer 160, +α is clockwise and −α is counter-clockwise. The polarization angle β is the twist rotation by the post-selection polarizer 210 about the exodus path 180. Looking down the beam 130 past the prism 170 towards the post-selection polarizer 210, +β is clockwise and −β is counterclockwise.

To achieve AAV amplification, the interaction of coherent photons in the light beam 130 with the TIR prism 170 must be weak and correspond to a weak measurement of the polarization difference operator $\hat{\Gamma}$. For this to occur, the weakness conditions must be satisfied. Because strength $$\gamma = \frac{1}{2}\Delta_{GH}$$

from eqn. (16) and weak polarization difference operator $$\Gamma_w = \cot\varepsilon \approx \frac{1}{\varepsilon},$$

such that $0<\varepsilon<<1$, eqn. (8) demonstrates that the constraint:

$$\Delta_{GH}<<4\Delta x\varepsilon, \quad (19)$$

is required for the sensor to AAV amplify the SPR enhanced GH shift.

Assuming that $\varepsilon=0.01$ radian and that the sensor'$\Delta x=260$ μm corresponds to the beam waist $\Delta x$ used in Jayaswal (2013), then AAV amplification is achieved when the constraint $\Delta_{GH}<<10.4$ μm=10,400 nm is satisfied. The GH shift constraint is consistent with the AAV amplified GH shifts (from 250 nm to 2500 nm) measured in Jayaswal (2013). Moreover, this constraint also shows that SPR enhanced GH shifts much smaller than those observed in Yin (2006) (between 39 μm and 44 μm) can be measured using the exemplary hybrid sensor.

As observed from eqn. (13) after AAV amplification, the translated intensity profile is attenuated by the factor:

$$|\langle \psi_{i}|\psi_{f}\rangle|^2=|\cos(\alpha-\beta)|^2 \quad (20)$$

so that when $$\alpha = \frac{\pi}{4}$$

and $\beta=-\alpha+\varepsilon$, such that $0<\varepsilon<<1$, the measured intensity is attenuated by the small factor:

$$|\langle \psi_i|\psi_f\rangle|^2=|\sin\varepsilon|^2\approx\varepsilon^2. \quad (21)$$

The combined component of the TIR prism 170 and the gold film 190 in the hybrid sensor becomes an ATR device by inducing SPR via the incident light beam 130. This further reduces the measured light intensity beyond the $\varepsilon^2$ attenuation produced by the nearly crossed pre- and post-selection polarizers 160 and 210. This combined attenuation can be obviated by selecting appropriate tradeoffs between input laser power, the ε angle selected, the thickness of the gold film 190 and the angle of the light.

The SPR enhanced GH shifts measured by Yin (2006) ranged between 39 μm and 44 μm. The non-SPR enhanced GH shifts measured by Jayaswal (2013) using the AAV effect ranged between 250 nm =0.25 nm and 2500 nm=2.5 μm. The hybrid biosensor should be able to measure SPR enhanced GH shifts two or three orders of magnitudes smaller than 10,400 nm=10.4 μm, i.e., in the range between 10.4 nm=0.0104 μm and 104 nm=0.104 μm.

This level of performance for the biosensor follows from the weakness condition constraint required to ensure that the measurement is weak —i.e., eqn. (18) when the hybrid biosensor is tuned to use typical values for the polarization angle difference ε and laser beam waist Δx.

Consequently, for angular difference $\varepsilon=0.01$ radian and beam waist $\Delta x=260$ μm, then the SPR enhanced GH shift must satisfy inequality $\Delta_{GH}<<10.4$ μm for the measurement to be weak and AAV amplification to occur. To observe how amplification is achieved, consider that when a weak measurement of an observable $\hat{\Gamma}$ is made and the photon states are pre- and post-selected, the mean pointer position shifts by $Y\Gamma_w$, where Y the interaction or coupling strength, and $\Gamma_w$ the weak value of observable $\hat{\Gamma}$ given by eqn. (11) in terms of the states.

Of course, simultaneous satisfaction of the two inequalities of eqn. (8) ensures that the measurement is a weak measurement. When the interaction Y is very small, then the interaction can be detected by increasing weak value $\Gamma_w$ to be large enough to observe the pointer shift—AAV amplification is used to detect strength Y. Specifically, AAV amplification occurs for weak measurements (i.e., $\Gamma_w>>1$) when the numerator in eqn. (11) is on the order of unity (i.e., $|\langle\psi_f|\hat{\Gamma}|\psi_i\rangle|\sim1$), and the denominator is small (i.e., $|\langle\psi_f|\psi_i\rangle|<<1$).

Also, because states $|\psi_i\rangle$, $|\psi_f\rangle$, and observable $\hat{\Gamma}$ are known, then the coupling strength y can be determined by dividing the measured pointer shift by the weak value $\Gamma_w$.

For the biosensor, the pre- and post-selected polarization states for the photons in the laser beam are given by respective eqns. (2) and (6), observable $\hat{\Gamma}$ is given by eqn. (5), and strength by eqn. (16). Applying these to eqn. (15) and using the specified settings for the polarizer angles α and β, so that the pre- and post-selected polarization states are ε radians away from being orthogonal, the pointer is shifted by $$\frac{1}{2}\Delta_{GH}\cot\varepsilon.$$

When $0<\varepsilon<<1$, then $\cot\varepsilon$ is large $$\left(i.e., \approx \frac{1}{\varepsilon}\right)$$

and AAV amplification occurs, thereby shifting the pointer through a detectable distance and heralding the presence of bio-molecules on the gold film 190 via the small SPR enhanced GH shift $\Delta_{GH}$.

Application to the general weakness conditions of eqn. (8) shows that both inequalities are satisfied and the biosensor is making weak measurements when eqn. (19) is satisfied. Substitution of typically used achievable values for ε (at 0.01 radian) and for the beam waist Δx (at 260 μm) into eqn. (19) shows that weak measurements and AAV amplification occur when GH shifts are considerably less than 10.4 μm. This defines the expected theoretical range of GH shifts that can be detected using AAV amplification (typically $10^{-2}$ to $10^{-3}$ times less than 10.4 μm). The size of the SPR enhanced GH shift varies directly with the concentration of bio-molecules adhering to the surface of the gold film 190—the higher the concentration, the larger the GH shift. Thus, using SPR enhanced GH shifts to detect the presence of bio-molecules adhering to the gold film 190 absent AAV amplification, enables detection of the smallest concentrations as producing (about) 39 μm GH shifts.

Although smaller concentrations nonetheless yield GH shifts, such shifts would not be detectable. However, by using exemplary MV amplification, such small GH shifts can be detected and measured—i.e., very small concentrations that produce otherwise undetectable GH shifts in the range 0.0104 μm to 0.104 μm. Because of this precision, the exemplary hybrid sensor can not only detect the presence of bio-molecules, but can also (when calibrated) measure the concentration. This aspect enables the exemplary apparatus to be useful for pharmaceutical applications and medical diagnostics.

An additional feature is that the hybrid sensor is easily modified to perform SPR enhanced GH shifts only—i.e., without AAV amplification. This is accomplished by simply removing the post-selection polarizer 210. This configuration can be useful when the concentration of bio-molecules adhering to the film are sufficiently large such that the GH shift is large and does not need AAV amplification for detection—i.e., the GH shift no longer satisfies the $\Delta_{GH} \ll 10.4$ μm constraint. In this case, the measurement is not weak, and thus maximum amplification would not be achieved (as post-selection is required for amplification).

Another feature is the option to scan the length of the entire reflecting side 250 of the prism 170 by translating that surface as per direction 260 (diagonal to the x and z directions. In this case the pointer estimator 240 would optionally produce a profile of the concentration distribution on the surface of the film 190. The gold film 190 and LMC 200 constitute necessary components of the detection process. Not only is the film 190 required for SPR, but it is effectively the part of the apparatus that tranduces the presence of bio-molecules adhering to its surface into an optical signal—i.e., a GH shift. The pointer 240 of the apparatus is the position of the mean intensity of the reflected laser beam 180 upon the face of the detector 230. The measured GH shift is the distance the mean intensity is translated from a zero position corresponding to the position of the mean intensity with absence of bio-molecules adhering to the gold film 190.

Equivalently, the GH shift effectively denotes the distance between the mean intensities of the p and s polarized parts of the beam 130. One may recall that $D_s \ll D_p$ and that the s polarized portion of the beam is not shifted by the SPR, and thus marks the zero position. The pointer estimator 240 determines the mean intensity location of the detector 230. The properties of the film 190 and the LMC 200 dictate which bio-molecules, compounds, and atoms will adhere to the film 190 for detection. Thus, the exemplary hybrid sensor described herein is a generic optical amplifier that renders detectable very small concentrations of any type or class of material that adheres to the film 190.

Subsequent inventions with different film structures and LMC devices expected to detect specific kinds of organic, inorganic and elemental substances are expected to follow in coming years to serve as transducers for the hybrid sensor described by this disclosure. These may include using this hybrid sensor architecture in chemical warfare, pharmaceutical, and medical diagnostics applications. To detect specific bio-molecules, (inorganic) molecules and atoms adhering to an adherent specific film, the laser wavelength, angle difference ε and beam waist Δx may be tuned to optimize the sensor performance for various applications.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. An optical biosensor for detecting a bio-molecular sample, said biosensor comprising:
   a laser source that emits a photon beam in an axial direction into an ambient medium;
   a collimating lens disposed along an incidence plane and normal to said axial direction to concentrate said beam;
   a pre-selection polarizer disposed normal to said beam to polarize said beam by pre-selection angle α about said axial direction thereby yielding a $|\psi_i\rangle$ pre-selective state, wherein $|\psi_i\rangle = \cos\alpha|s\rangle + \sin\alpha|p\rangle$ such that $|p\rangle$ and $|s\rangle$ are orthonormal photon linear polarization states corresponding respectively to parallel and perpendicular directions relative to said incidence plane arid orthogonal to said axial direction;
   an optical right-isosceles prism having a dielectric constant greater than said ambient medium, said prism including incident and exodus sides perpendicular to each other and an opposite diagonal side, said beam entering said prism through said incident side, reflecting by said diagonal side and exiting towards said vertical direction through said exodus side;
   a metal film disposed on said diagonal side to provide surface plasmon resonance (SPR) amplification of a Goos-Hänchen (GH) effect;
   a liquid medium containing the sample, said medium being disposed along said metal film opposite said diagonal side;
   a post-selection polarizer disposed normal to said lateral direction to polarize said beam by post-selection angle β about said lateral direction thereby yielding a $|\psi_f\rangle$ post-selective state, wherein $|\psi_f\rangle = \cos\beta|s\rangle + \sin\beta|p\rangle$;
   a photon detector for detecting said beam to obtain weak value $$\Gamma_w = \frac{\langle\psi_f|\hat{\Gamma}|\psi_i\rangle}{\langle\psi_f|\psi_i\rangle} \gg 1$$

of a polarization difference operator $\hat{\Gamma} = |s\rangle\langle s| - |p\rangle\langle p|$, thereby enabling Aharonov-Albert-Vaidman (AAV) amplification; and
   a pointer estimator for measuring a sample mean intensity, to determine a GH shift $\Delta_{GH}$ that translates a sample pointer for said sample mean intensity from a zero position corresponding to a reference mean intensity absent the sample on said metal film.

2. The sensor according to claim 1, further comprising:
   a first slit screen disposed between said laser and said collimating lens perpendicular to said axial direction to direct said beam; and
   a second slit screen disposed between said post-selection polarizer and said detector perpendicular to said lateral direction to direct said beam.

3. The sensor according to claim 1, wherein said metal film is gold.

4. The sensor according to claim 1, wherein said detector is a charge coupled device.

5. The sensor according to claim 1, wherein said detector is a split detector.

6. An optical biosensor for detecting a bio-molecular sample, said biosensor comprising:
- a laser source that emits a photon beam in an axial direction into an ambient medium;
- a collimating lens disposed perpendicular to said axial direction to concentrate said beam;
- a pre-selection polarizer disposed normal to said beam to polarize said beam by pre-selection angle α about said axial direction;
- an optical right-isosceles prism having a dielectric constant greater than said ambient medium, said prism including incident and exodus sides perpendicular to each other and an opposite diagonal side, said beam entering said prism through said incident side, reflecting by said diagonal side and exiting towards a lateral direction through said exodus side;
- a metal film disposed on said diagonal side to provide surface plasmon resonance (SPR) amplification of a Goos-Hänchen (GH) effect;
- a liquid medium containing the sample, said medium being disposed along said metal film opposite said diagonal side;
- a post-selection polarizer disposed normal to said lateral direction to polarize said beam post-selection angle β about said lateral direction;
- a photon detector for detecting said beam; and
- a pointer estimator for measuring a sample mean intensity to determine a GH shift $\Delta_{GH}$ that translates a sample pointer for said sample mean intensity from a zero position corresponding to a reference mean intensity absent the sample on said metal film, wherein said pre-selection polarizer has angle $$\alpha = \frac{\pi}{4}$$

and said post-selection polarizer has angle, β=−α=ϵ, where deviation angle is defined as 0<ϵ<<1.

7. The sensor according to claim 6, wherein said photon beam has a beam waist Δx, such that said GH shift corresponds to $\Delta_{GH} << 4\Delta x \epsilon$.

8. An optical biosensor for detecting a bio-molecular sample, said biosensor comprising:
- a laser source that emits a photon beam in an axial direction into an ambient medium;
- a collimating lens disposed normal to said axial direction to concentrate said beam;
- a pre-selection polarizer disposed normal to said beam to polarize said beam by pre-selection angle α about said axial direction;
- an optical right-isosceles prism having a dielectric constant greater than said ambient medium, said prism including incident and exodus sides perpendicular to each other and an opposite diagonal side, said beam entering said prism through said incident side, reflecting by said diagonal side and exiting towards a lateral direction through said exodus side;
- a metal film disposed on said diagonal side to provide surface plasmon resonance (SPR) amplification of a Goos-Hänchen (GH) effect;
- a liquid medium containing the sample, said medium being disposed along said metal film opposite said diagonal side;
- a post-selection polarizer disposed normal to said lateral direction to polarize said beam by post-selection angle β about said lateral direction;
- a photon detector for detecting said beam; and
- a pointer estimator for measuring a sample mean intensity to determine a GH shift $\Delta_{GH}$ that translates a sample pointer for said sample mean intensity from a zero position corresponding to a reference mean intensity absent the sample on said metal film, wherein said detector obtains weak value $$\Gamma_w = \frac{\langle \psi_f | \hat{\Gamma} | \psi_i \rangle}{\langle \psi_f | \psi_i \rangle} >> 1$$

of a polarization difference operator $\hat{\Gamma}$, such that $|\psi_i\rangle$ and $|\psi_f\rangle$ denote respective pre- and post-selective states, thereby enabling Aharonov-Albert-Vaidman (AAV) amplification, said pre-selection polarizer has angle $$\alpha = \frac{\pi}{4}$$

and said post-selection polarizer has angle β=−α+ϵ, where deviation angle is defined as 0<ϵ<<1, and said weak value equals cotangent of said deviation angle such that $\Gamma_w$=cot ϵ.

* * * * *